United States Patent
Single

(10) Patent No.: US 7,529,587 B2
(45) Date of Patent: May 5, 2009

(54) EXTERNAL SPEECH PROCESSOR UNIT FOR AN AUDITORY PROSTHESIS

(75) Inventor: Peter Scott Single, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 439 days.

(21) Appl. No.: 10/962,441

(22) Filed: Oct. 13, 2004

(65) Prior Publication Data

US 2005/0078846 A1 Apr. 14, 2005

(30) Foreign Application Priority Data

Oct. 13, 2003 (AU) ............................... 2003905570

(51) Int. Cl.
*A61N 1/00* (2006.01)
(52) U.S. Cl. .................................................. 607/57
(58) Field of Classification Search ............. 607/55–57; 600/25; 381/312
See application file for complete search history.

(56) References Cited

U.S. PATENT DOCUMENTS

| | | | |
|---|---|---|---|
| 4,756,312 A * | 7/1988 | Epley ........................... | 607/57 |
| 5,176,620 A * | 1/1993 | Gilman ......................... | 600/25 |
| 5,313,557 A | 5/1994 | Osterhout | |
| 5,609,616 A * | 3/1997 | Schulman et al. ............. | 607/56 |
| 6,073,050 A | 6/2000 | Griffith | |
| 6,711,271 B2 * | 3/2004 | Hou ........................... | 381/323 |
| 6,785,397 B2 * | 8/2004 | Arnstein ...................... | 381/423 |
| 6,904,156 B1 * | 6/2005 | LeReverend ................ | 381/312 |
| 6,920,226 B2 * | 7/2005 | Sauer ......................... | 381/312 |
| 7,346,397 B2 * | 3/2008 | Money et al. ................. | 607/57 |

OTHER PUBLICATIONS

Nagarajan, Devanand, Examiner's First Search Report on Australian patent application No. 2004218723, Nov. 7, 2008, 2 pages, Australia.

* cited by examiner

*Primary Examiner*—Mark W Bockelman
(74) *Attorney, Agent, or Firm*—Connolly Bove Lodge & Hutz LLP

(57) ABSTRACT

A speech processor unit (12) for a cochlear implant system. The speech processor unit (12) comprises a signal processor for processing incoming auditory signals and for forwarding processed signals to an implanted component (18) of the system, a monitoring means for monitoring a predetermined parameter, and a controller, controlled by the signal processor, for placing the unit in an idle state in the absence of the parameter. The predetermined parameter can comprise the presence or absence of the implanted receiver antenna coil (22) relative to the external antenna coil (16). The invention allows the speech processor unit (12) to be supplied without a physical on and off switch.

21 Claims, 4 Drawing Sheets

EXTERNAL SPEECH PROCESSOR UNIT FOR AN AUDITORY PROSTHESIS

CROSS-REFERENCE TO RELATED APPLICATIONS

The present application claims priority from Provisional Patent Application No 2003905570 filed on Oct. 13, 2003, the contents of which is incorporated herein by reference.

BACKGROUND

1. Field of the Invention

This invention relates to a speech processor unit for an auditory prosthesis. More particularly, the invention relates to an external speech processor unit for a cochlear implant system.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often helped by use of conventional hearing aids which amplify sound so that acoustic information reaches the cochlea and the hair cells.

In many people who are profoundly deaf, however, the reason for their deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to, or absence of, the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Typically, cochlear implant systems consist essentially of two components, an external component commonly referred to as a processor unit and an internal, implanted component commonly referred to as a stimulator/receiver unit, the latter receiving signals from the processor unit to provide the sound sensation to a user.

The external component includes a microphone for detecting sounds, such as speech and environmental sounds, a speech processor that converts speech into a coded signal, a power source such as a battery, and an external transmitter coil.

The coded signal output by the sound processor is transmitted transcutaneously to the implanted stimulator/receiver unit situated within a recess of the temporal bone of the user. This transcutaneous transmission occurs via the external transmitter antenna coil which is positioned to communicate with an implanted receiver antenna coil of the stimulator/receiver unit. Therefore, the communication serves two essential purposes; firstly to transmit, transcutaneously, the coded signal and, secondly, to provide power to the implanted stimulator/receiver unit. The transcutaneous link is, normally, in the form of a radio frequency (RF) link, but other such links have been proposed and implemented with varying degrees of success.

The implanted stimulator/receiver unit includes, in addition to the receiver antenna coil that receives the coded signal and power from the external processor component, a stimulator that processes the coded signal and outputs a stimulation signal to an intracochlea electrode assembly which applies the electrical stimulation directly to the auditory nerve producing a hearing sensation corresponding to the originally detected sound.

The external component is carried on the body of the user, such as in a pocket of the user's clothing, a belt pouch or in a harness, while the microphone is mounted on a clip mounted behind the ear or on the lapel of the user.

More recently, the physical dimensions of the sound processor have been able to be reduced allowing for the external component to be housed in a relatively small unit capable of being worn discreetly behind the ear of the user. The external transmitter antenna coil is still positioned on the side of the user's head to allow for the transmission of the coded sound signal and power from the sound processor to the implanted stimulator unit.

Such behind the ear units (BTEs) have provided a degree of freedom and subtlety for the recipient which has not traditionally been possible with body worn devices. There is no longer a need for extensive cables connecting the body worn processor to the transmitter antenna coil, nor is there a need for a separate microphone unit or battery pack, as the BTE unit contains all the components in one housing.

One common feature of all BTE units is the provision of a dedicated mechanical switch for turning the unit on or off. Such a switch is typically small in size and difficult to manipulate, especially in the case of elderly recipients or those who are not very dexterous. Continuous use of the switch causes mechanical fatigue resulting in the switch failing to operate and requiring repair or replacement.

A further problem with BTE devices of current designs is that the area around the switch permits the ingress of moisture that can damage or destroy the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to the invention, there is provided a speech processor unit for a cochlear implant system, the speech processor unit comprising:

a signal processor for processing incoming auditory signals and for forwarding processed signals to an implanted component of the system;

a monitoring means for monitoring a predetermined parameter; and a controller, controlled by the signal processor, for placing the unit in an idle state in the absence of the parameter.

The unit may include a microphone for receiving external auditory signals and for feeding these signals to the signal processor.

The microphone may be connected to a pre-amplifier and an analogue-to-digital converter (ADC). The pre-amplifier and ADC may be implemented as a single module which may normally draw power supplied by a bias circuit. The bias circuit may have a power down control operable under the control of the signal processor.

As is the case with a conventional external speech processor unit, the unit may include a data encoder/formatter which is used to send stimulation commands to an implanted component of the cochlear implant. The implanted component, or implant, may include an implanted receiver and a stimulator unit. The stimulator unit may feed received signals to an electrode array arranged in a cochlea of a recipient.

The formatter may communicate with the implanted component via a transcutaneous inductive link. Thus, the formatter may feed signals in the form of stimulation commands, being coded sound signals, and power signals via a transmitter antenna coil arranged externally of the recipient's body.

This link may also be used to receive messages from the implanted component which may be fed back via the formatter to the signal processor.

The unit may further include a memory and a battery supply for supplying power to the unit. To reduce power consumption of the unit, the signal processor (which may be a digital signal processor), the data encoder/formatter and the memory may be implemented by way of CMOS circuitry.

In one embodiment of the invention, the parameter monitored by the unit may be the presence of the implanted component. The monitoring means may therefore be implemented as a part of the digital signal processor. Thus, the digital signal processor may, periodically, send an interrogation signal to determine if the implanted component is present. It will be appreciated that, should the external unit have been removed from the recipient's body, normally behind the recipient's ear, the implanted component will not be detected by the digital signal processor. This may be taken as an indication that the external component is not being used, for example, due to the recipient being asleep or in a situation where the cochlear implant is not being used, for example, while bathing, etc.

In such circumstances, the digital signal processor may disable the bias circuit causing the preamplifier and ADC module to enter a low power state. The digital signal processor may also stop sending commands to the implanted component and may stop accessing memory, the latter step causing the memory to stop drawing power.

Finally, the signal processor may send a "pause" signal to the controller which interrupts a clock signal from an oscillator to the signal processor. In this state, all CMOS circuits are idle and only the oscillator and the controller may draw power.

The unit may remain in this state for a predetermined delay period, the delay period being generated by the controller. A typical value may be about 1 second. When the delay is complete, the clock signal to the signal processor may be resumed. The signal processor may then send a further command to the implanted component. Assuming the implanted component is still not detected and the signal processor receives no response, the signal processor may immediately re-enable the controller.

The controller may be a pause-and-gate circuit. The pause-and-gate circuit may be implemented either as hardware or as software in the signal processor. In the latter case, the function of the pause-and-gate circuit may be performed by the signal processor.

Further, the signal processor may include a set of event counters for timing real-time-events. These event counters may be suitable for implementing the pause-and-gate function whereby the counters may generate an interrupt signal when they have run for their pre-allocated time. This interrupt may start the signal processor running again.

In another embodiment of the invention, the parameter monitored by the unit may be motion of the recipient. Thus, the unit may include a motion-detecting means. The motion-detecting means may operate the pause-and-gate circuit of the unit. The motion-detecting means may be in the form of a mercury switch. In the absence of motion, the switch may cause the unit to enter an idle state.

In yet a further embodiment of the invention, the parameter being monitored may be a value of reflected impedance as "seen" by the signal processor. When the receiver antenna coil has been removed, the reflected impedance as detected by the signal processor may be much higher than when the receiver antenna coil is present. Thus, by appropriate calculation to take into account current drawn during stimulation and the current drawn by the components of the unit itself, the signal processor can determine whether or not the implanted component is present. If not, the signal processor may follow substantially the same procedure as described above with reference to the first embodiment.

BRIEF DESCRIPTION OF THE DRAWINGS

The invention is now described by way of example with reference to the accompanying drawings in which.

DETAILED DESCRIPTION

Figure 1:
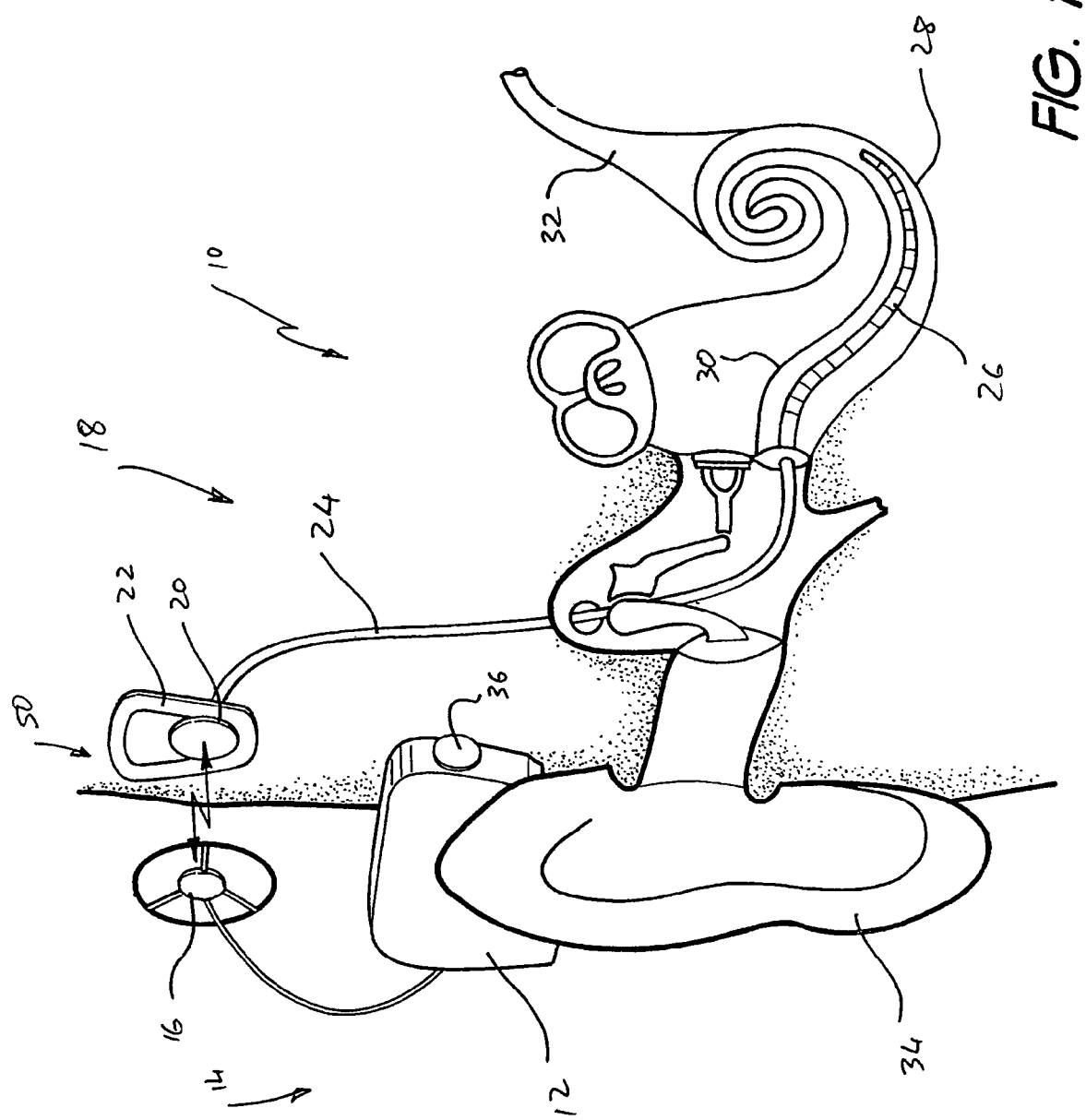
FIG. 1 shows a schematic representation of a cochlear implant system, in accordance with an embodiment of the invention.

Referring initially to FIG. 1 of the drawings, reference numeral 10 generally designates a cochlear implant system including an external speech processor 12, in accordance with the invention. The system 10 includes an external component 14 made up of the speech processor 12 and a transmitting device, in the form of a transmitter antenna coil 16, and an internal component, or implant, 18. The internal component 18 includes an implanted receiver and stimulator unit 20 implanted in a recess in a temporal bone of a recipient. The stimulator unit 20 receives signals from an implanted receiver antenna coil 22. The stimulator unit 20 is connected via a conductor or lead 24 to an intracochlea electrode array 26 mounted in the cochlea 28 of the recipient. The received signals are therefore applied by the electrode array 26 to the basilar membrane 30 of the recipient and nerve cells within the cochlea 28 to effect stimulation of the auditory nerve 32 to provide a hearing sensation for the recipient.

In one implementation of the system 10, the external speech processor unit 12 is of sufficiently small dimensions to be mounted behind an outer ear 34 of the recipient. The external speech processor unit 12 includes a microphone 36 for detecting sounds such as speech and surrounding environmental sounds.

Figure 2:
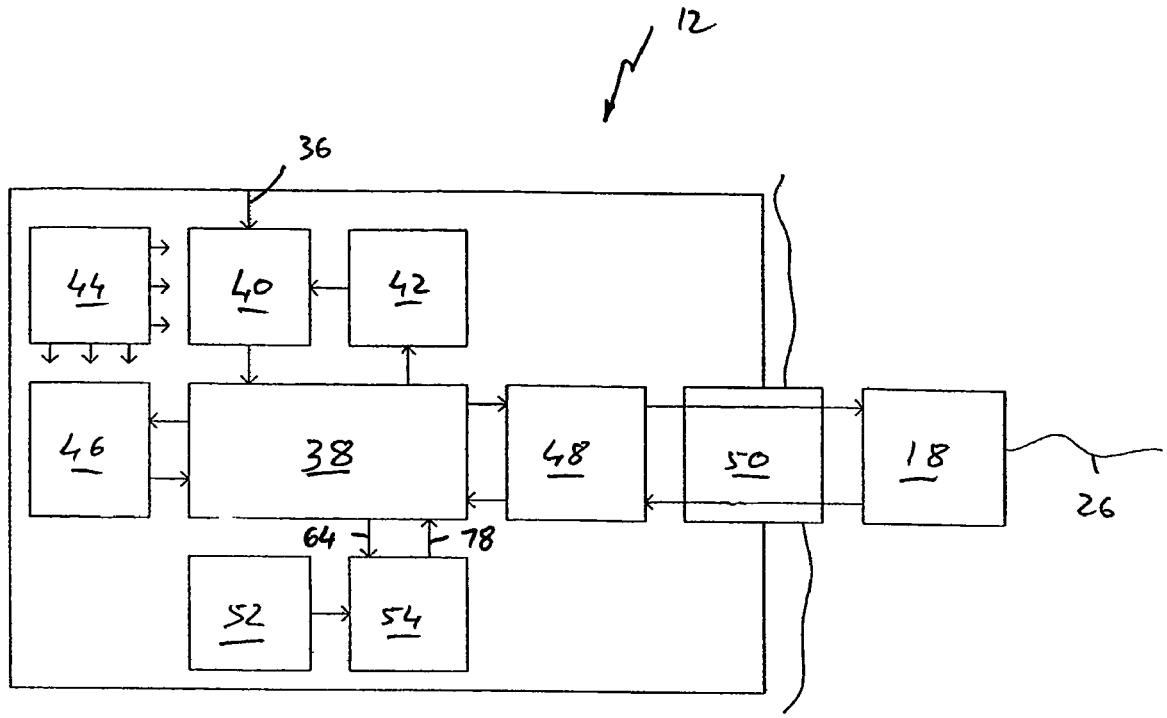
FIG. 2 shows a block diagram of an external speech processor unit, in accordance with the invention, for the implant of FIG. 1.

Referring now to FIG. 2 of the drawings, a block diagram of the external speech processor unit 12 is shown in greater detail. The processor unit 12 comprises a digital signal processor 38. Auditory inputs from the microphone 36 are fed to a pre-amplifier and ADC module 40. The module 40 is controlled by a bias circuit 42. The bias circuit 42 has a power-down control. When the power-down control is activated, the module 40 ceases operation. When the module 40 ceases operation it is put in a mode which draws only a relatively minute amount of power.

The unit 12 is powered by a set of internal batteries 44. It is a desire of the industry to reduce power consumption so that the batteries 44 require replacement as infrequently as possible.

Further, the unit 12 includes a memory 46. The memory 46 contains psychophysical data, such as threshold and comfort levels of the recipient as mapped from each of the electrodes of the electrode array 26.

Data from the signal processor 38 are fed to a data encoder/formatter 48. The formatter 48 is used to send stimulation commands and power across a transcutaneous link 50 to the implant 18 of the system 10. The transcutaneous link 50 is made up of the transmitter antenna coil 16 of the external component 14 and the receiver antenna coil 22 of the implant 18.

The signal processor 38 is also formatted to interrogate the implant 18 and to receive messages back from the implant 18 via the formatter 48. When stimulation commands are to be sent by the signal processor 38 to the implant 18, the information is encoded by the formatter 48 into a coded signal, being stimulation commands representative of the sound signal received from the microphone 36.

The signal processor 38 analyses received sound signals from the microphone 36. The received sound signals are split up into frequency bands in accordance with the tonotopic arrangement of the electrodes of the array 26. The signal processor 38 analyses the amplitude of the signals in each discrete frequency band in accordance with a specific sound processing strategy. For example, the signal processor 38 can detect the "n" largest outputs for each filter channel, measure the amplitude of each filter channel and rank them accordingly.

Following frequency analysis and processing of the sound signals, the signal processor 38 can access data allocating each frequency band to an electrode pair of the electrode array 26 from the memory 46. Using this information, the sound signal is mapped to a recipient's electrode array 26 by selecting the electrodes assigned to the particular frequency and choosing a level between comfort and threshold to represent the loudness of that frequency component.

The unit 12 includes an oscillator 52. The oscillator 52 generates a master clock signal 78 for the entire unit 12.

The speech processor unit 12 is, where applicable, made using CMOS circuitry for all digital circuits and, more particularly, the signal processor 38, the formatter 48 and the memory 46. In addition, the oscillator 52 is a CMOS design which draws approximately 100 μA or less.

The oscillator feeds its output to a pause-and-gate circuit 54. The circuit 54 consists of a low-power counter that gates the clock from the oscillator 52 to the signal processor 38. In a normal operating mode the circuit 54 passes the clock signal 78 from the oscillator 52 to the signal processor 38 and, from there, to the rest of the speech processor unit 12. In a pause mode, the circuit 54 interrupts the clock signal 78 to the signal processor 38 and waits for a delay signal from the signal processor 38. The signal processor 38 controls when the pause-and-gate circuit 54 enters its pause mode.

Figure 5:
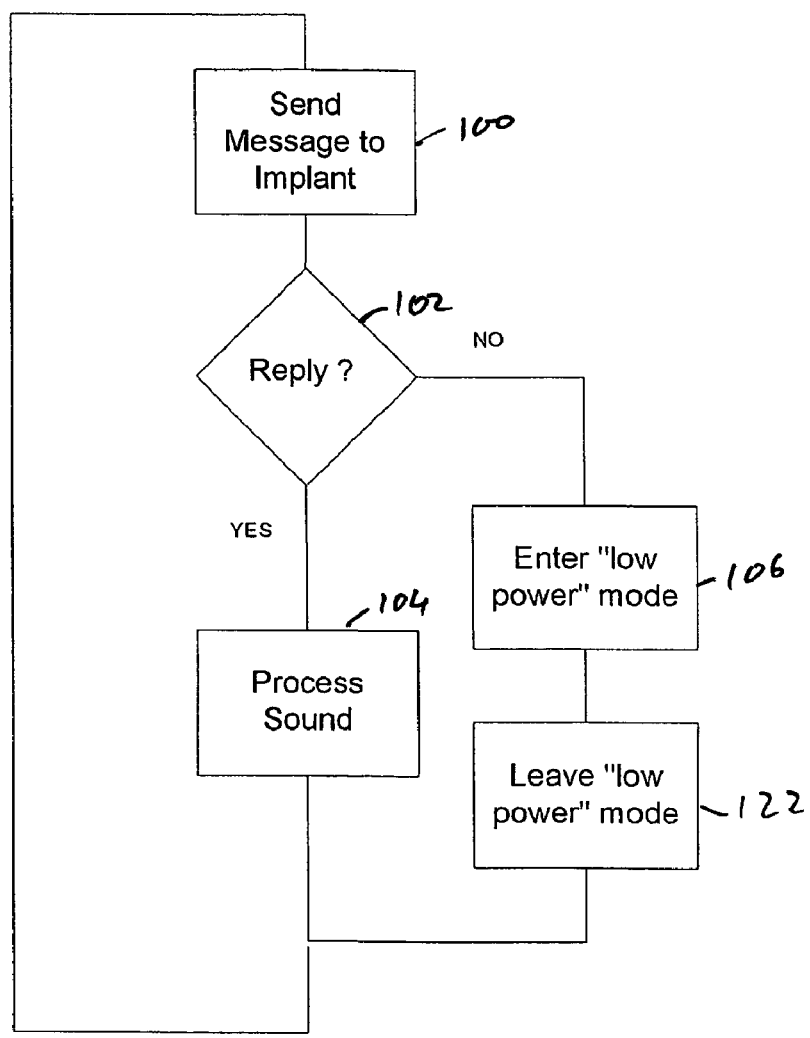
FIG. 5 shows a flow chart of the operation of the unit of FIG. 2.
Figure 6:
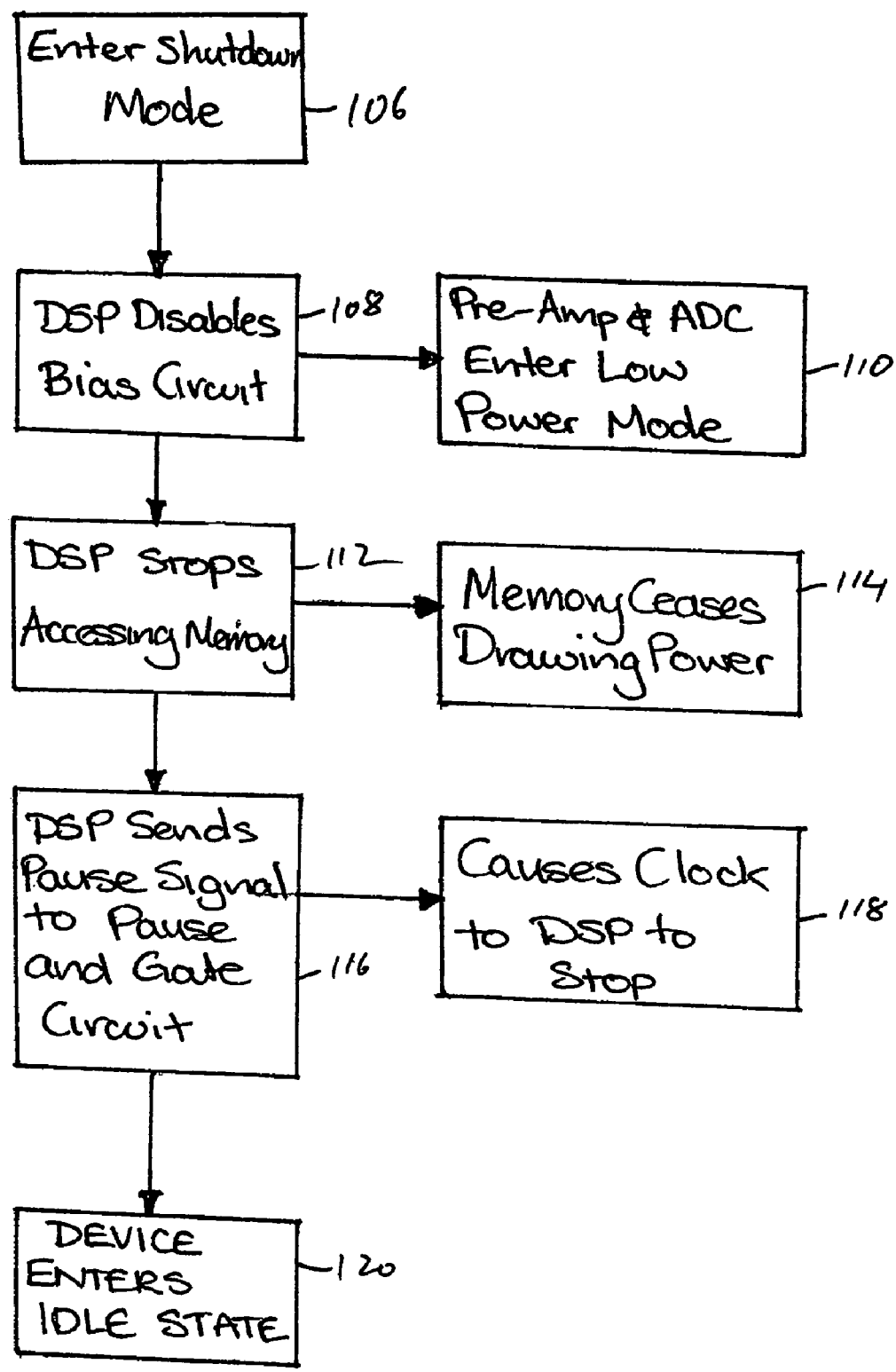
FIG. 6 shows a flow chart of the unit being placed in an idle mode.

The external speech processor unit 12 operates as follows. The operation is described with reference to FIGS. 5 and 6 of the drawings. It is assumed that the system 10 is operating normally and processing sound. All circuits of the external speech processor unit 12 are active. Periodically, for example, once every 10 seconds, the signal processor 38 polls the implant 18 with a message that includes a telemetry command at step 100 in FIG. 5 and awaits a reply 102. If the signal processor 38 receives a response from the implant 18, it "knows" that the implant 18 is present and continues processing sound 104. If, however, the signal processor 38 does not receive a telemetry response, it can send one or more telemetry commands to the implant 18 to detect if its receiving antenna coil 22 is present. After confirming that the receiving antenna coil 22 is not present, the speech processor unit 12 assumes that this is because the receiving antenna coil 22 is not in communication with the transmitting antenna coil 16 of the external component 14. This is taken as a message to "switch off", i.e. to enter an idle state as shown at step 106 (FIGS. 5 and 6).

The signal processor 38 (or "DSP") then starts its shut-down routine as described with reference to FIG. 6 of the drawings. This routine initially involves disabling the bias circuit 42 at step 108. Disabling the bias circuit 42 causes the pre-amplifier and ADC module 40 to enter a low-power state as shown 110. The signal processor 38 also stops sending commands to the implant 18 and stops accessing the memory 46 at step 112.

When the signal processor 38 stops accessing the memory 46, this causes the memory 46 to stop drawing power from the batteries 44 as shown at 114.

Finally, the signal processor 38 sends a "pause" signal, via a pause input 64 (see FIG. 4) to the pause-and-gate circuit 54 at step 116. This causes the circuit 54 to enter its pause mode whereby the clock signal 78 from the oscillator 52 to the signal processor 38 is interrupted as shown at 118.

In this state, all CMOS circuits are in an idle state 120. The oscillator 52 and the pause-and-gate circuit 54 continue to draw power from the batteries 44 but no other components do or, more accurately, the power drawn is so small as to be relatively negligible. In this state, the power drawn by the unit 12 is that drawn by the oscillator 52 and is typically less than 100 μA.

The unit 12 remains in this state for the delay generated by the pause-and-gate circuit 54. A typical value for this delay is of the order of about 1 second. When this delay is completed, the clock signal 78 from the oscillator 52 to the signal processor 38 is re-applied by the pause-and-gate circuit 54 to the signal processor 38. The signal processor 38 then sends a telemetry command to the implant 18 as shown at 122 in FIG. 5 of the drawings. Assuming the implant 18 is still not present, the signal processor 38 will receive no response. This causes the signal processor 38 to instruct the pause-and-gate circuit 54 to enter its pause mode once again.

The unit 12 can remain in this mode for any time period ranging from minutes to many hours as long as the transmitter antenna coil 16 is not placed on the recipient's head which would re-establish the transcutaneous link 50 to the implant 18. Thus, if the recipient has placed the transmitter antenna coil 16 in register with the receiver antenna coil 22, the link 50 is re-established. Thus when the signal processor 38 again sends a detection command to the implant 18, it will receive a response. It then knows that it has to start processing sound again. In this configuration, the signal processor 38 re-enables the pre-amplifier and ADC module 40, waits a short time for any analogue circuitry to stabilise and recommences sound processing.

A typical speech processor unit 12 draws between 2-25 mA when operating. For the sake of the example, it is assumed that the current drawn is 15 mA on average. It is also assumed that it takes 1 ms for the speech processor to re-activate, send a telemetry command, receive a reply and shut down again. Thus, with a signal processor 38 with a 10 MHz clock, this allows 1000 instructions for operation which is well within the capabilities of a standard signal processor 38. In its idle state, the unit 12 draws approximately 100 µA. Thus, the average current drawn by the speech processor unit 12 is approximately 105 µA. This is sufficiently low that a battery could provide this power for a long period of time. A typical battery has a capacity of 300 mAH. Thus, the processor unit 12 can operate for nearly 3000 hours in this mode.

Figure 4:
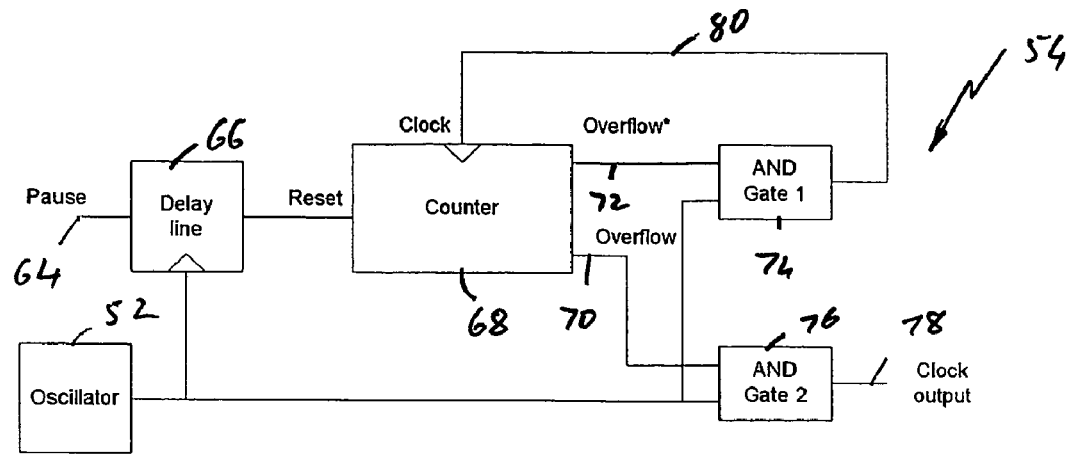
FIG. 4 shows a block diagram of the pause-and-gate circuit of FIG. 2.

An implementation of the pause-and-gate circuit 54 is shown in FIG. 4 of the drawings. The circuit 54 has a pause input 64 that, as described above, is asserted by the signal processor 38 when it has failed to detect the implant 18 and so initiates the low-power routine. A delay module 66 allows the DSP clock signal 78 to continue while the signal processor 38 clears the pause input 64 to prevent the unit 12 from locking up.

Further, as indicated above, the oscillator 52 provides the clock signal 78 for the signal processor 38 and a clock signal 80 for a counter 68 of the pause-and-gate circuit 54.

The counter 68 sets the time for the "idle" state for the unit 12. The counter 68 has two outputs, an "Overflow" output 70 and an "Overflow*" output 72. The "Overflow" output 70 is asserted when the count has reached its maximum value. The "Overflow*" output 72 is the logical inverse of "Overflow" output 70. An AND gate 74 gates the "Overflow*" output 72 and the oscillator 52 to provide the clock signal 80 for the counter 68. A second AND gate 76 gates the "Overflow" output 70 and the oscillator 52 to provide the clock signal 78 for the signal processor 38.

The circuit 54 operates in the following manner. Under normal operating conditions, when the implant 18 is detected, the oscillator 52 is running and the Overflow output 70 is high. This allows the clock signal 78 to toggle and drive the signal processor 38. The "Overflow*" output 72 is low so the AND gate 74 prevents the oscillator 52 clocking the counter 68.

To enter the low-power state, the signal processor 38 sets the pause signal 64. This initiates a pulse in the delay module 66. The signal processor 38 then resets the pause signal 64. The delay module 66 has as many stages as the number of clock cycles required by the signal processor 38 to clear the pause signal 64 to allow the pause signal 64 to be reset.

A pulse from the delay module 66 resets the counter 68. Resetting of the counter 68 causes the "Overflow" output 70 going low which, in turn, results in the clock signal 78 to the signal processor 38 being inhibited by AND gate 76. The "Overflow*" output 72 goes high so the oscillator 52 clocks the counter 68 via the AND gate 74. The counter 68 has sufficient stages that it can count for the time for which the unit 12 must be in its low-power state. At the end of this time, when the counter 68 has reached its maximum count value, the "Overflow" output 70 goes high, allowing the clock signal 78 to the signal processor 38 to resume. The "Overflow*" output 72 goes low blocking the clock signal 80 to the counter 68. The clock signal 78 is then available to the signal processor 38, allowing it to check for the presence of the implant 18.

In a variation of the invention, the pause-and-gate circuit 54 can be implemented as software in the signal processor 38 if the signal processor 38 is configured to run a software timer at sufficiently low power.

Further, if the signal processor 38 has a set of event counters for timing real-time events, these might be suitable for implementing the pause-and-gate function. These counters generate an interrupt when they have run for the pre-allocated time. The interrupt starts the signal processor 38 running again.

Figure 3:
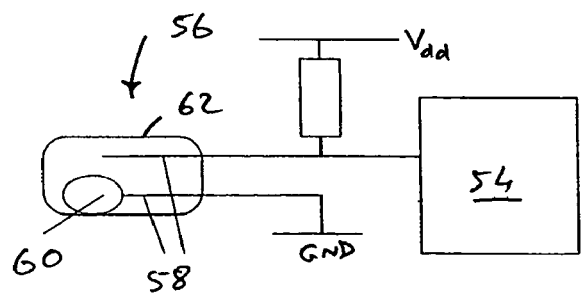
FIG. 3 shows a block diagram of another embodiment of part of the unit.

In another embodiment of the invention, illustrated in FIG. 3 of the drawings, the speech processor unit 12 includes a motion detecting mechanism in the form of a motion detecting switch 56. The motion detecting switch 56 is connected to the pause-and-gate circuit 54. In the absence of motion for a predetermined period of time, the switch 56 causes the pause-and-gate circuit 54 to enter its pause mode interrupting the clock signal 78 from the oscillator 52 to the signal processor 38. This causes the unit 12, in the absence of the implant 18 to enter its idle state, as described above.

Conveniently the motion switch 56 is a mercury switch having a pair of contacts 58 which, when the switch 56 is closed, is bridged by a blob of mercury 60. The contacts 58 and mercury 60 are housed in an envelope 62 of a non-conductive material, such as glass. The switch 56 is arranged so that, in the absence of motion, the mercury 60 does not bridge the contacts 58, thereby disabling the switch 56. Movement of the recipient is required to move the mercury 60 so that it bridges the contacts 58. When this occurs, the pause-and-gate circuit 54 enters it normal mode.

Thus, as long as the external component 14 of the implant 12 is left idle, for example, on a bedside table during the night while the recipient is a sleep the speech processor unit 12 will remain in its idle mode. If the unit 12 is, for example, bumped then the signal processor 38 will be activated, but detect that the implant 18 is absent and the unit 12 will again be placed in its idle state.

Yet a further embodiment of the invention relies on reflected impedance. In this embodiment of the invention, the reflected impedance of the implant receiver antenna coil 22 affects the input impedance of the transmitter antenna coil 16 as detected by the signal processor 38. This embodiment operates in a similar manner to the implementation described above with reference to FIG. 2 of the drawings except that the signal processor 38 measures current used to drive the implant 18.

For this embodiment of the invention, the battery 44 has a small resistor in series forming an ammeter so that the signal processor 38 can measure the supply current.

Since the supply current of the speech processor unit 12 varies with the stimulation rate, the signal processor 38 must compensate for the rate at which it is sending radio frequency (RF) signals across the link 50 the implant 18. For this purpose the signal processor performs the following steps:
  records the rate at which it sends RF frames to the implant 18;
  measures the current drawn from the battery 44 using the ammeter;
  subtracts from the values measured, the current drawn by the signal processor 38 itself, the analogue circuitry etc.;
  from the previous step, calculates the power drawn from the battery 44 for each stimulation;
  from the calculation in the preceding step, determines whether or not the implant 18 is present.

Typically, when the signal processor 38 is driving the implant 18 it draws a current of about 12 mA maximum. When the receiver coil 22 is absent, the drawn current can reach levels of up to 80 mA. As a result, this large difference in values means that errors from the ammeter or from the calculation are not critical.

Accordingly, it is an advantage of the invention that a cochlear implant system 10 is provided which omits a mechanical on/off switch in the external processor. Such a mechanical switch is prone to failure as it is used many times by the recipient. In addition, because of the small size of behind the ear external speech processor units 12, the switch itself is also of small dimensions. This makes it difficult for older people or less dexterous people to manipulate such switches. Because the invention obviates the need for a switch, this problem is also overcome.

In addition, one of the causes of failures of external speech processor units 12 is the ingress of moisture. Often the ingress of moisture is through the aperture in a casing of the external speech processor unit for a lever of an on/off switch. Once again, because the on/off switch is able to be eliminated in the present invention, this problem is also, to at least a large extent, overcome. Thus, this renders the system 10 more versatile as it is now possible for recipients to use the system 10 even in wet environments such as when showering or out in the open and being caught in the rain.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A cochlear implant comprising:
    an internal component comprising:
        a receiver configured to receive signals, and
        a stimulator configured to output stimulation signals based on said signals received by said receiver,
    an external component comprising:
        an acoustic transducer configured to convert a received acoustic signal into an electrical signal,
        a signal processor configured to convert said electrical signal into a coded signal,
        a transmitter configured to transmit said coded signal to said receiver, and
        a monitor configured to determine if said external component is in proximity to said internal component,
    wherein said signal processor is configured to place said external component in an idle state of reduced power consumption when said monitor determines that said external component is not in proximity to said internal component.

2. The cochlear implant of claim 1, wherein said transmitter is configured to transmit a telemetry command to said internal component, and wherein said monitor is configured to determine if said external component is in proximity to said internal component based on the response by said internal component to said telemetry command.

3. The cochlear implant of claim 2, wherein in the absence of a response by said internal component to said telemetry command said monitor is configured to determine that said external component is not in proximity to said internal component.

4. The cochlear implant of claim 1, wherein said monitor is configured to determine if said external component is in proximity to said internal component by measuring the impedance between said signal processor and said internal component.

5. The cochlear implant of claim 1, wherein said external component further comprises:
    a module having a pre-amplifier and an analog-to-digital converter (ADC), said module configured to receive said electrical signal output of said acoustic transducer; and
    a bias circuit configured to control the supply of power to said module,
    wherein said signal processor is configured to place said external component into said idle state by disabling the supply of power from said bias circuit to said module.

6. The cochlear implant of claim 1, wherein said signal processor is configured to place said external component into said idle state by disabling the transmission of said coded signals by said transmitter.

7. The cochlear implant of claim 1, wherein said external component further comprises:
    a battery supply for supplying power to one or more components of said external component, and
    wherein said signal processor is configured to place said external component into said idle state by disabling the supply of power from said battery supply to said one or more components.

8. The cochlear implant of claim 1, wherein said external component further comprises:
    a memory configured to store psychophysical data of a recipient of said cochlear implant, and wherein said signal processor is configured to place said external component into said idle state by disabling access to said memory.

9. The cochlear implant of claim 1, wherein said external component further comprises:
    a controller operable under the control of said signal processor; and
    an oscillator configured to deliver a clock signal to said signal processor,
    wherein said signal processor is configured to send a pause signal to said controller so as to interrupt said clock signal from said oscillator to said signal processor when said monitor determines that said external component is not in proximity to said internal component.

10. The cochlear implant of claim 9, wherein said controller is a pause-and-gate circuit.

11. The cochlear implant of claim 1, wherein said monitor is implemented as a module of said signal processor.

12. A cochlear implant comprising:
    an internal component comprising:
        a receiver configured to receive signals, and
        a stimulator configured to output stimulation signals based on said signals received by said receiver,
    an external component comprising:
        an acoustic transducer configured to convert a received acoustic signal into an electrical signal,
        a signal processor configured to convert said electrical signal into a coded signal,
        a transmitter configured to transmit said coded signal to said receiver, and
        a monitor configured to detect motion of the external component;
    wherein said signal processor is configured to place said external component in an idle state of reduced power consumption when said monitor determines that said external component has ceased movement.

13. The cochlear implant of claim 12, wherein said monitor comprises a mercury switch.

14. The cochlear implant of claim 12, wherein said signal processor is configured to place said external component in an idle state of reduced power consumption after said speech processor has ceased movement for a period of time.

15. The cochlear implant of claim 12, wherein said external component further comprises:

a module having a pre-amplifier and an analog-to-digital converter (ADC), said module configured to receive said electrical signal output of said acoustic transducer; and a bias circuit configured to control the supply of power to said module, wherein said signal processor is configured to place said external component into said idle state by disabling the supply of power from said bias circuit to said module.

16. The cochlear implant of claim 12, wherein said signal processor is configured to place said external component into said idle state by disabling the transmission of said coded signals by said transmitter.

17. The cochlear implant of claim 12, wherein said external component further comprises:

a battery supply for supplying power to one or more components of said external component, and wherein said signal processor is configured to place said external component into said idle state by disabling the supply of power from said battery supply to said one or more components.

18. The cochlear implant of claim 12, wherein said external component further comprises:

a memory configured to store psychophysical data of a recipient of said cochlear implant, and wherein said signal processor is configured to place said external component into said idle state by disabling access to said memory.

19. The cochlear implant of claim 12, wherein said external component further comprises:

a controller operable under the control of said signal processor; and an oscillator configured to deliver a clock signal to said signal processor, wherein said signal processor is configured to send a pause signal to said controller so as to interrupt said clock signal from said oscillator to said signal processor when said monitor determines that said external component has ceased movement.

20. The cochlear implant of claim 19, wherein said controller is a pause-and-gate circuit.

21. The cochlear implant of claim 12, wherein said monitor is implemented as a module of said signal processor.

\* \* \* \* \*